(12) United States Patent
Maruta et al.

(10) Patent No.: US 6,410,016 B2
(45) Date of Patent: *Jun. 25, 2002

(54) METHOD FOR ADMINISTERING VIABLE MICROORGANISM COMPOSITION FOR POULTRY

(75) Inventors: Kiyoshi Maruta; Hiroshi Miyazaki, both of Kanagawa (JP)

(73) Assignee: Calpis Co., LTD, Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/424,986

(22) PCT Filed: Jun. 2, 1998

(86) PCT No.: PCT/JP98/02440

§ 371 (c)(1),
(2), (4) Date: Dec. 3, 1999

(87) PCT Pub. No.: WO98/54981

PCT Pub. Date: Dec. 10, 1998

(30) Foreign Application Priority Data

Jun. 3, 1997 (JP) .............................. 9-145372

(51) Int. Cl.$^7$ .............................. A01N 63/00; C07C 1/02
(52) U.S. Cl. .............................. 424/93.45; 424/93.462; 424/93.1; 424/93.46; 424/93.3; 435/262.5; 435/262
(58) Field of Search .............................. 424/93.21, 93.3, 424/93.46, 93.45, 93.1, 93.462; 435/262.5, 262

(56) References Cited

U.S. PATENT DOCUMENTS

| 4,950,256 A | * | 8/1990 | Luther et al. ................ 604/265 |
| 5,296,221 A | * | 3/1994 | Mitsuoka et al. .............. 424/93 |
| 5,340,577 A | * | 8/1994 | Nisbet et al. ............. 424/93.21 |
| 5,534,253 A | * | 7/1996 | Casas et al. ............. 424/93.45 |
| 5,603,930 A | | 2/1997 | Brassart et al. |

FOREIGN PATENT DOCUMENTS

| EP | 0 287 699 A | 10/1988 |
| WO | WO 92 12639 A | 8/1992 |
| WO | WO 92 12723 A | 8/1992 |
| WO | WO 96 39862 A | 12/1996 |

* cited by examiner

*Primary Examiner*—Jon P. Weber
*Assistant Examiner*—Patricia D Patten
(74) *Attorney, Agent, or Firm*—Oblon, Spivak, McClelland, Maier & Neustadt, P.C.

(57) ABSTRACT

A method for administering viable microorganism compositions for poultry, comprising: administering a viable microorganism composition comprising viable lactic acid bacteria belonging to *Lactobacillus reuteri* and *Lactobacillus johnsonii* at the stage of newborn fledgling; and administering a viable microorganism composition which comprises a viable microorganism belonging to *Bacillus subtilis*.

23 Claims, No Drawings

ID: 6,410,016 B2

METHOD FOR ADMINISTERING VIABLE MICROORGANISM COMPOSITION FOR POULTRY

The present application claims priority under 35 U.S.C. §371 to PCT/JP98/0240 filed Jun. 2, 1998.

TECHNICAL FIELD

The present invention relates to a method for administrating viable microorganism compositions to poultry in which viable microorganism compositions useful for the growth of poultry are administered, thereby feeding the poultry with a high productivity while reducing the amounts of medicaments, such as antibiotics, antibacterial agents and the like, or without the administration of the medicaments.

BACKGROUND ART

In the feeding of poultry, such as broilers and the like, dense rearing of 40 to 60 birds per 1 tsubo (ca. 3.3 m$^2$) of a poultry farm is generally carried out in order to reduce the production cost. Furthermore, poultry is fed in to achieve rapid growth, 40 to 55 g in average daily body weight gain, so that the birds may be shipped by about 2 months after hatching. Under these conditions, the poultry is always under great stress, and they often become sick, and diseases often spread among the poultry. In floor feeding, since the poultry pecks the feed and the like, which are smeared with excrement on the floor, toxic bacteria spread very easily upon all the birds in the feeding facility. Also, in an open feeding facility, or even in a windowless feeding facility in some cases, toxic bacteria can easily spread across the feeding facility. In addition, for example, although a broiler house is disinfected every time when broilers are shipped, since small animals, such as rats and the like, in the surrounding area are not affected by this treatment, and these animals carry bacteria, such as salmonella and the like, into the poultry house when broiler chicks are again put into the feeding facility.

In order to maintain high productivity while preventing a decrease in the rate of growth and the like during the feeding period, and also to prevent the contamination of the poultry with toxic bacteria under these conditions, various medicaments, such as antibiotics, antibacterial agents and the like, are generally administered to the poultry.

However, since these exists the possibility of residual medicaments in the meat and eggs, and also the danger of generating bacterial strains resistant to the medicaments (as has actually been reported in many cases), demand has been increasing among users for drug-free livestock farm products, produced without using medicaments.

On the other hand, under natural conditions without dense rearing of a large number of poultry, high productivity cannot be expected. However, it is possible to raise poultry, such as chickens and the like, without using medicaments, such as antibiotics, antibacterial agents and the like. The meat and eggs of chicken raised under natural conditions, namely so-called yard native chicken, are now in great demand because of the safety and good taste, and traded on the market at a high price.

Consequently, great interest has been directed toward the development of a feeding method for raising poultry, such as chickens and the like, without causing contamination with toxic bacteria, while maintaining high productivity, by a drug-free feeding method (feeding in which medicaments, such as antibiotics, antibacterial agents and the like, are not used during part of, or through the entire, period of feeding, so that the medicaments do not remain in the birds, at least at the time of shipping).

When the conventional dense rearing of large numbers of poultry is carried out by merely avoiding the administration of medicaments, the poultry are easily infected with toxic bacteria. Therefore it is not possible to maintain productivity at a commercially acceptable level without causing contamination with toxic bacteria.

As a means for reducing the infection of poultry with toxic bacteria without depending on medicaments, such as antibiotics, antibacterial agents and the like, it has been proposed to administer microorganisms and the like which are useful for the growth of various poultry. Bacteria belonging to the genus Bacillus, lactic acid bacteria belonging to the genus Lactobacillus, bacteria belonging to the genus Bifidobacterium and the like are known as useful microorganisms for feed additive or as various CE (competitive exclusion) preparations. Some of these microorganisms are commercially available as feed additive viable microorganism preparations for poultry. However, although the effects are recognized to some extent, they are not sufficient. Particularly, no means has been reported which can carry out drug-free feeding of poultry in dense rearing, with a large number of poultry, and with productivity at a commercially acceptable level by providing these viable microorganism preparations.

For example, Japanese Registered Patent No. 2528055 and JP-B-3-79988 (the term "JP-B" as used herein means an "examined Japanese patent application") disclose that body weight gain and feed conversion ratios in animals can be improved and effects, such as intestinal function controlling action and the like, can be obtained by administering a viable microorganism preparation comprising *Bacillus subtilis* to animals. It is possible to carry out drug-free feeding by applying the means to, for example, broilers, but only in a certain limited regions where broilers are not produced on a large scale. However, in many regions where broiler feeding is frequently carried out, since they are often infected with toxic bacteria which spread easily through the feeding facilities as described above, it is extremely difficult to carry out commercial drug-free feeding of broilers using this means. Also, even if drug-free feeding of broilers using this means were possible, the body weight gain rate of the poultry is slower than feeding using medicaments. As a result, the high productivity of the drug-applied feeding is not obtained.

In addition, the viable microorganism preparations currently on the market have problems, such as the reduction of the viable count during the distribution steps, the poor colonization ability after the formation of intestinal bacterial flora, the necessity for the continued administration of the viable microorganism preparations for a prolonged period of time, and the like. Particularly, the necessity for the continued administration of the viable microorganism preparations for a prolonged period of time, due to the poor colonization ability after the formation of intestinal bacterial flora, is presently a serious obstacle to the practical use from the viewpoints of economics.

DISCLOSURE OF THE INVENTION

An object of the present invention is to provide a method for administrating viable microorganism compositions to poultry, so that drug-free feeding of poultry can be carried while maintaining good productivity.

For resolving the above-mentioned problems, the inventors of the present invention have carried out screening of useful bacteria from broad natural sources, and have found that certain lactic acid bacteria isolated from the intestinal tract of a chicken can be easily colonized in the intestinal tract of newborn chickens shortly after hatching. Also, the inventors have found that particularly a heterofermentation lactic acid bacterium isolated from the ileum of a chicken and a homofermentation lactic acid bacterium isolated from the cecum of a chicken can easily be colonized on the intestinal tract of newborn fledglings and have various effects, such as inhibition of the growth of toxic bacteria, prevention of diarrhea, enhancement of growth, improvement of the rate of raising, improvement of the feed conversion ratios and the like. In addition, the inventors have found that lactic acid bacteria can be colonized on the intestinal tract of newborn chicks soon after their birth by merely spraying a suspension of viable microorganisms of these lactic acid bacteria of the genus Lactobacillus only once to newborn chicks within 4 days after hatching.

Furthermore, the inventors have found that, when useful lactic acid bacteria are colonized in combination with the administration of *Bacillus subtilis* viable microorganisms during a period from the fledgling stage to the mature bird state in the drug-free feeding of poultry, body weight gain at the initial feeding stage can be improved and a sufficient rate of raising can be obtained in comparison with the single administration of *Bacillus subtilis* viable microorganisms, so that it becomes possible to carry out drug-free feeding of poultry by dense rearing in a large number of poultry with commercially effective high productivity. The present invention has been accomplished on the basis of these findings.

Thus, the present invention relates to a method for administering viable microorganisms to poultry, comprising:

administering a first composition to a poultry comprising viable bacteria belonging to *Lactobacillus reuteri* and *Lactobacillus johnsonii*, at the stage of newborn fledgling.

Furthermore, the present invention relates to a method for administering viable microorganism compositions for poultry, comprising:

administering a viable microorganism composition for poultry comprising viable lactic acid bacteria belonging to *Lactobacillus reuteri* and *Lactobacillus johnsonii* at the stage of newborn fledgling; and administering a viable microorganism composition for poultry comprising a viable microorganism belonging to *Bacillus subtilis*.

BEST MODE FOR CARRYING OUT THE INVENTION

The method of the present invention for administrating viable microorganism compositions for poultry, includes a viable microorganism composition for poultry comprising viable lactic acid bacteria belonging to *Lactobacillus reuteri* and *Lactobacillus johnsonii* (hereinafter often referred to as a "viable microorganism composition of lactic acid bacteria") is administered to newborn fledglings.

The above-described lactic acid bacteria belonging to the genus Lactobacillus are facultative anaerobic bacteria. Not only those isolated from the intestinal tract of poultry but also other strains isolated from a natural source can be used effectively. Preferred examples of the strain belonging to *Lactobacillus reuteri* include *Lactobacillus reuteri* CP-720 (Deposit No. FERM BP-6332), *Lactobacillus reuteri* CP-722 (Deposit No. FERM BP-6334) and the like. Preferred example of the strain belonging to *Lactobacillus johnsonii* includes *Lactobacillus johnsonii* CP-721 (Deposit No. FERM BP-6333) and the like. These three strains have been deposited at National Institute of Bioscience and Human-Technology, Agency of Industrial Science and Technology (Address: 1–3, Higashi 1 chome, Tsukuba-shi, Ibaraki-ken 305-8566, Japan) on Apr. 27, 1998. Other strains of *Lactobacillus reuteri* and *Lactobacillus johnsonii* are known, such as those described in *ATCC Bacteria and Bacteriophages*, 19th ed., 1996, pages 195 and 197, hereby incorporated by reference.

Bacteriological properties of *Lactobacillus reuteri* CP-720 and CP-722 and *Lactobacillus johnsonii* CP-721 are shown in Table 1.

TABLE 1

| Bacteriological property | CP-720 | CP-721 | CP-722 |
|---|---|---|---|
| (Morphological property) | | | |
| 1) Shape of cells | rod | rod | rod |
| 2) Presence of mobility | no | no | no |
| 3) Presence of spores | no | no | no |
| 4) Gram staining | positive | positive | positive |
| (Physiological property) | | | |
| 1) Catalase | − | − | − |
| 2) Formation of indole | − | − | − |
| 3) Behavior against oxygen | facultative anaerobe | facultative anaerobe | facultative anaerobe |
| 4) Growth at 15° C. | − | − | − |
| 5) Growth at 45° C. | + | + | + |
| 6) Optical rotation of lactic acid | DL | DL | DL |
| 7) Generation of gas | + | − | + |
| 8) Formation of acid from saccharides | | | |
| glucose | + | + | + |
| lactose | + | + | + |
| mannose | − | − | − |
| fructose | + | + | + |
| galactose | + | + | + |
| sucrose | + | + | + |
| arabinose | + | − | + |
| maltose | + | + | + |
| cellobiose | − | + | − |
| rhamnose | ± | − | ± |
| xylose | + | − | + |
| trehalose | ± | − | ± |
| melibiose | + | + | + |
| raffinose | + | + | + |
| mannitol | − | − | − |
| sorbitol | − | − | − |
| esculin | − | + | − |
| salicin | − | + | − |
| starch | + | + | + |

The viable microorganism composition of lactic acid bacteria may further contain heterofermentation lactic acid bacteria belonging to the genus Lactobacillus other than *Lactobacillus reuteri*, such as *Lactobacillus brevis, Lactobacillus buchneri* and the like, and also homofermentation lactic acid bacteria belonging to the genus Lactobacillus other than *Lactobacillus johnsonii*, such as *Lactobacillus gasseri, Lactobacillus crispatus* and the like, belonging to the *Lactobacillus acidophillus* group. Many different strains of many different genera of Lactobacillus are known, such as those described in *ATCC Bacteria and Bacteriphages*, 19th ed., 1996, pages 192–199, hereby incorporated by reference.

Preferred examples of the medium which can be used in culturing the viable microorganisms of lactic acid bacteria include a milk medium, such as cow's milk, goat's milk, horse's milk and the like, skim milk thereof and a medium for lactic acid bacteria, such as BL medium, Briggs liver broth medium, MRS medium, GAM medium, TTY medium and the like.

The lactic acid bacteria can be cultured at 25 to 45° C., more preferably 30 to 40° C., and for 6 to 30 hours, more preferably 10 to 24 hours. The culture broth thus obtained can be used directly as the viable microorganism composition of lactic acid bacteria by storing as such at about 5° C. until use. Alternatively, the microorganisms may be recovered by centrifugation, mixed with a protective agent and then freeze-dried in vacuo. The resulting powder of the bacteria can be stored in a cool and dark chamber and used as a viable microorganism composition of lactic acid bacteria by suspending, mixing or dissolving the powder when used. The powder of dry microorganisms prepared in this manner is more preferred because it can withstand long periods of storage.

The viable microorganism composition of lactic acid bacteria may contain a carrier and diluent. The carrier and diluent are not particularly limited, and selected from pharmaceutically or nutritionally acceptable carriers and diluents. Also, the viable microorganism composition of lactic acid bacteria may be contain a poultry feed (ration).

In the present invention, the microorganisms belonging to *Lactobacillus reuteri* and *Lactobacillus johnsonii* may be subjected to an appropriate mutation treatment, such as exposure to ultraviolet light, X-ray or radiation, and a chemical treatment with a mutagenic compound (e.g., nitrsoguanidine, acridine dye). Mutants may also be prepared by insertion, deletion or substitution of nucleotides, as well as spontaneous mutation. The terms *Lactobacillus reuteri* and *Lactobacillus johnsonii* include these mutants.

The term "stage of newborn fledgling" means just after hatching of the fledgling (e.g., chick, poult, squab or the like), specifically a period of 0 to about 4 days after hatching. The time for the administration of the viable microorganism composition of lactic acid bacteria is not particularly limited so long as during the stage of newborn fledgling; however, it is preferred to administer the composition within 4 days after hatching, more preferably within 2 days after hatching, a period before colonization of intestinal bacterial flora in the intestinal tract of the fledgling. The number of times of the administration is not particularly limited; however, sufficient effects can generally be obtained by a single administration. The effects obtained become more stable and secure as the number of times of administration increases. However, administration three times or more is not economical, and the effects obtained thereby are almost the same as administration two times.

Although not particularly limited, administration of the viable microorganism composition of lactic acid bacteria can be carried out by oral administration. Specifically, the composition can be orally administered by adding it to drinking water or the like and allowing fledglings to ingest it freely, or by spraying it from a position above the fledglings using a spray or the like. The spray administration method is preferred because of the habit of fledglings to chirp while opening their beaks upwards so that the viable microorganism composition having a high concentration can be orally administered at the stage of newborn fledgling easily and securely.

In carrying out the administration, the total density of lactic acid bacteria in the viable microorganism composition of lactic acid bacteria is preferably from $10^6$ to $10^{10}$ viable microorganisms per g, more preferably from $10^7$ to $10^9$ viable microorganisms per g. In addition, the viable microorganism composition of lactic acid bacteria is preferably administered in an amount of $1\times10^3$ to $1\times10$ viable microorganisms per fledgling, more preferably $1\times10^4$ to $1\times10^6$ viable microorganisms per fledgling.

In the method of the present invention, a viable microorganism composition for poultry comprising a viable microorganism belonging to *Bacillus subtilis* (hereinafter often referred to as a "viable microorganism composition of *Bacillus subtilis*") is administered in addition to the above-described administration of the viable microorganism composition of lactic acid bacteria.

Preferred examples of the strain of *Bacillus subtilis* include *Bacillus subtilis* C-3102 (Deposit No. FERM BP-1096) which has been deposited in Institute of Bioscience and Human-Technology (old name: Fermentation Research Institute), Agency of Industrial Science and Technology (Address: 1–3, Higashi 1 chome, Tsukuba-shi (old address: Yatabe-machi, Tsukuba-gun), Ibaraki-ken 305-8566 (old zip code: 305), Japan) on Jun. 28, 1986, and the like. Bacteriological properties of *Bacillus subtilis* C-3102 are already described in Japanese Registered Patent No. 2528055, JP-B-3-79988 and U.S. Pat. No. Re. 34,837. Many different strains of *Bacillus subtilis* are known, such as those described in *ATCC Bacteria and Bacteriophages*, 19th ed., 1996, pages 57–63, hereby incorporated by reference.

In culturing of *Bacillus subtilis* C-3102, an aqueous or solid medium containing materials, such as carbon sources, nitrogen sources, inorganic substances and the like, which are generally used in culturing of microorganisms can be used as the culture medium. Examples of the carbon sources include those which can be assimilated, such as glucose, fructose, sucrose, starch, molasses and the like. Examples of the nitrogen sources include peptone, meat extract, casein hydrolysate, ammonium sulfate and the like. As occasion demands, phosphates, salts of magnesium, potassium, sodium, calcium, iron, manganese and the like, vitamins, amino acids, antifoaming agents, surfactants and the like can further be added as inorganic components. Culturing is preferably carried out aerobically. The starting pH of the medium is preferably 5 to 9, more preferably 6 to 8; the culture temperature is preferably 20 to 50° C., more preferably 35 to 40° C.; and the culturing period is preferably 12 hours to 7 days.

The culture mixture obtained in this manner can be used as the viable microorganism composition of *Bacillus subtilis* as such or as its concentrated product or as cells isolated therefrom, directly or after adding additives such as fillers and the like. The fillers are not particularly limited, and examples include calcium carbonate, defatted rice bran, corn grits, corn flour, wheat bran, skim milk powder and the like.

The viable microorganism composition of *Bacillus subtilis* may be contain a carrier or diluent. The carrier and diluent are not particularly limited, and selected from pharmaceutically or nutritionally acceptable carriers and diluents. Also, the viable microorganism composition of *Bacillus subtilis* may be contain a poultry feed.

In the present invention, the microorganism belonging to *Bacillus subtilis* may be subjected to an appropriate mutation treatment, such as exposure to ultraviolet light, X-ray or radiation, and a chemical treatment with a mutagenic compound (e.g., nitrsoguanidine, acridine dye). Mutants may also be prepared by insertion, deletion or substitution of nucleotides, as well as spontaneous mutation. The term *Bacillus subtilis* includes these mutants.

The time of the administration of the viable microorganism composition of *Bacillus subtilis* is not particularly limited; however, in order to obtain appropriate colonization of intestinal bacterial flora, it is preferred to administer the viable microorganism composition of *Bacillus subtilis* after the administration of the above-described viable microorganism composition of lactic acid bacteria. Also, in the case of a feeding method in which antibiotics, antibacterial agents and the like are not administered during a period between the newborn fledgling stage and the finishing stage, it is preferred to administer the viable microorganism composition of *Bacillus subtilis* during that period. In the case of broiler feeding, for example, it can be administered during an optional period between the newborn fledgling stage and the finishing stage; however, when a drug-free feeding is carried out only during the grower stage and finishing stage so that the medicaments do not remain in the body of the broiler at the time of broiler shipping, the viable microorganism composition of *Bacillus subtilis* can be administered during the grower stage and finishing stage.

Administration of the viable microorganism composition of *Bacillus subtilis* can be carried out by oral ingestion after adding it to feed, drinking water or the like.

For example, when the viable microorganism composition of *Bacillus subtilis* containing *Bacillus subtilis* C-3102 is mixed with feed in carrying out the administration, it is preferred that the feed has a microorganism density of $10^5$ to $10^8$ viable microorganisms per gram in the form of spores and/or vegetable cells.

The method of the present invention for administering the viable microorganism compositions for poultry can be applied not only to chickens to be fed under dense rearing in a large number of birds but also to chickens to be fed under other conditions and to other domestic birds such as ducks, geese, quails, wild ducks, ostriches and the like, as well as pet birds and the like.

When the viable microorganism compositions for poultry are administered in the above-described method, an intestinal bacterial flora in which useful bacteria for the growth of poultry predominate can be formed in the intestines, so that the poultry grows in good health. Various effects, such as growth inhibition of toxic bacteria, prevention of diarrhea, enhancement of growth, improvement of the feed conversion ratios and the like, can be obtained, and drug-free feeding of chickens becomes possible. Also, since useful bacteria dominate the intestinal bacterial flora, the poultry grow in good health, so that delicious meat, eggs and the like can be obtained in the case of edible poultry due to markedly improved qualities of the products. In addition, the meat, eggs and the like are safe, and are not contaminated with toxic food poisoning bacteria.

EXAMPLES

Having generally described this invention, a further understanding can be obtained by reference to certain specific examples which are provided herein for purposes of illustration only and are not intended to be limiting unless otherwise specified.

PRODUCTION EXAMPLE 1

A 4.5 g portion of skim milk was dissolved in 50 g of water, pasteurized at 100° C. for 10 minutes and then cooled to room temperature. One loopful of *Lactobacillus reuteri* CP-720 was inoculated into the thus prepared solution and cultured statically for 24 hours at 37° C. to obtain a first starter (lactic acid bacteria: $1\times10^8$ viable microorganisms per gram). Next, 15 g of the first starter was inoculated into 500 g of skim milk (solid content, 9% by weight) which had been pasteurized at 90° C. and cultured for 20 hours at 37° C. to obtain a second starter. The second starter contained $2\times10^8$ viable microorganisms per gram.

A medium prepared by dissolving 200 g of casein peptone, 200 g of yeast extract, 100 g of sodium citrate and 200 g of glucose in 20 kg of water and adjusting the pH of the medium to 7.0 with 1 N sodium hydroxide solution was put into a jar fermentor, pasteurized at 95° C. for 15 minutes and then cooled to room temperature. Thereafter, 3 parts by weight of the above-described second starter was inoculated into 100 parts by weight of the medium and cultured statically for 20 hours at 37° C.

The thus obtained culture broth was centrifuged to recover the microorganisms which were subsequently freeze-dried using, as a dispersion medium, 1 kg of a solution containing 10% by weight of skim milk and 1% by weight of sodium glutamate, which had been pasteurized at 90° C. in advance, thereby obtaining 146 g of *Lactobacillus reuteri* CP-720 viable microorganism powder. The viable microorganism powder contained $7.0\times10^{10}$ viable microorganisms per gram.

PRODUCTION EXAMPLE 2

A medium prepared by dissolving 200 g of beef peptone, 60 g of soybean peptone, 100 g of yeast extract, 100 g of sodium acetate, 40 g of dipotassium phosphate, 60 g of diammonium citrate and 400 g of glucose in 20 kg of water and adjusting the pH of the medium to 7.0 with 1 N sodium hydroxide solution was put into a jar fermentor, pasteurized at 95° C. for 15 minutes and then cooled to room temperature. Thereafter, 500 g of a second starter of *Lactobacillus johnsonii* CP-721 which had been pre-cultured in advance by the same procedure of Production Example 1 was inoculated into the medium to carry out 18 hours of standing culture at 35° C.

The thus obtained culture broth was centrifuged to harvest the microorganisms which were subsequently freeze-dried using, as a dispersion medium, a solution containing 10% by weight of skim milk and 1% by weight of sodium glutamate, which had been pasteurized at 90° C. in advance, thereby obtaining 141 g of *Lactobacillus johnsonii* CP-721 viable microorganism powder. The microorganism powder contained $6.5\times10^{10}$ viable microorganisms per gram.

PRODUCTION EXAMPLE 3

A second starter of *Lactobacillus reuteri* CP-722 prepared by the same procedure of Production Example 1 was inoculated into a medium prepared and pasteurized in the same manner as described in Production Example 1 having the same composition and weight of components, and cultured statically for 20 hours at 37° C. The thus obtained culture broth was centrifuged to collect the cells which were subsequently freeze-dried using, as a dispersion medium, a solution containing 10 wt % skim milk and 1 wt % sodium glutamate, which had been pasteurized at 95° C. in advance, thereby obtaining 151 g of *Lactobacillus reuteri* CP-722 viable microorganism powder. The viable microorganism powder contained $6.8\times10^{10}$ viable microorganisms per gram.

PRODUCTION EXAMPLE 4

The viable microorganism powders obtained in Production Examples 1 to 3 were combined in one part portions and thoroughly mixed with 7 parts of dextrin to obtain a viable microorganism composition of lactic acid bacteria for poultry containing three lactobacillus strains. The viable microorganism composition contained $2.0\times10^{10}$ viable microorganisms per gram.

PRODUCTION EXAMPLE 5

A medium prepared by dissolving 200 g of soybean peptone, 10 g of dipotassium phosphate and 200 g of molasses in 10 kg of water and adjusting the medium pH to 7.5 with 1 N sodium hydroxide solution was put into a jar fermentor, pasteurized at 95° C. for 60 minutes and then cooled to 37° C. Thereafter, 100 g of a culture broth of *Bacillus subtilis* C-3102 which had been pre-cultured in advance was inoculated into the medium and stirred aerobically for 40 hours at 37° C. The thus obtained culture broth was centrifuged to recover the microorganisms which were subsequently mixed with the same weight of skim milk and freeze-dried in vacuo, thereby obtaining 750 g of the viable microorganism composition of *Bacillus subtilis* for poultry. The *Bacillus subtilis* viable microorganism composition for poultry contained $1.2 \times 10^{10}$ viable microorganisms per gram.

EXAMPLE 1

Field effect test I (test with no drugs in and after the grower stage)

The test was carried out using Chunky (Brand Name, Commercial strain). Chicks (0 day after hatching) in a chick-carrying cage were spray-provided with 12 g of the viable microorganism composition of lactic acid bacteria for poultry prepared in Production Example 4 (total number of lactic acid bacteria: $2.0 \times 10^{10}$ viable microorganisms per gram) which had been uniformly suspended in 4 kg of pure water. As the provision feed, "Chick Prestarter Feed (Hina Ezuke)" for starter feed use (containing antibiotics) and "Starting AT (Zenki AT)" for starting stage use (containing antibiotics) were used in the start feeding stage (from 0 to 5 days after hatching) and starting stage (from 5 to 21 days after hatching), respectively. "Brogoal A" for finishing use (containing no antibiotics) which had been mixed with $9 \times 10^5$ cells/g of the viable microorganism composition of *Bacillus subtilis* for poultry prepared in Production Example 5 was used during the period from the grower stage (from 21 days to 43 days after hatching) to the finishing stage (from 43 days to the day of shipping) (all of these commercial feed articles are manufactured by Chubu Shiryo). Other feed management was carried out in accordance with the feeding method of chickens conventionally carried out in poultry farms. The results of the test are shown in Table 2.

COMPARATIVE EXAMPLE 1

Feeding was carried out in the same manner as in Example 1, except that the administration of the viable microorganism composition of lactic acid bacteria was not carried out, a "Grower AT (Kohki AT)" for grower stage use (containing antibiotics) (manufactured by Chubu Shiryo, Co.) was used as the feed in the grower stage instead of the "Brogoal A" for finishing use, and the viable microorganism composition of *Bacillus subtilis* was not provided throughout the whole stages. The results are shown in Table 2. In this connection, the "Grower AT (Kohki AT)" is a feed article having the same composition as that of the "Brogoal A" except for antibiotics.

TABLE 2

| | Comp. Example 1 | Example 1 | Ratio |
|---|---|---|---|
| The number of set chicks | 8,250 | 8,250 | 100 |
| Body weight of chicks (g/chick) | 41.9 | 38.4 | 92 |
| The number of birds shipped | 7,721 | 7,830 | 101 |
| Age when shipped (days) | 54 | 55 | 102 |
| The number of chicks per tsubo | 58.9 | 58.9 | 100 |
| Average body weight (kg/birds) | 2.766 | 2.797 | 101 |
| Rate of raising (%)* | 93.59 | 94.91 | 101 |

TABLE 2-continued

| | Comp. Example 1 | Example 1 | Ratio |
|---|---|---|---|
| Feed conversion ratio** | 2.061 | 2.055 | 100 |
| Production score*** | 233 | 235 | 101 |
| Body weight gain (g/day · chick) | 51.22 | 50.86 | 99 |

*Rate of raising: (the number of birds shipped/the number of set chicks) × 100
**Feed conversion ratio: (total amount of feed ingested during feeding (g)/total body weight gain (g)) × 100
*** Production score: (average body weight × rate of raising/feed conversion ratio × age in days when shipped) × 100

The value of average body weight gain in Example 1 was smaller than that of Comparative Example 1 by a factor of about 1%, which was assumed to be due to the quality of chicks tested. That is, the body weight of chicks was standard (41.9 g/chick) in Comparative Example 1 but was close to that of junior chicks (38.4 g/chick) in Example 1, so that their growth became inferior. Since other results of Example 1 were superior to those of Comparative Example 1, the productivity was improved.

EXAMPLE 2

Field effect test II (test with no drugs in and after the starting stage)

The test was carried out using Chunky (Brand name, Commercial strain). Chicks (0 day after hatching) in a chick-carrying cage were spray-provided with 12 g of the viable microorganism composition of lactic acid bacteria for poultry prepared in Production Example 4 (total number of lactic acid bacteria: $2.0 \times 10^{10}$ viable microorganisms per gram) which had been uniformly suspended in 4 kg of pure water. As the provision feed, the "Chick Prestarter Feed" for starter feed use was used in the start feeding stage (from 0 to 5 days after hatching). "Starting AT (Zenki AT)" for starting stage use from which antibiotics had been removed and the "Brogoal A" for finishing use, which had been mixed with $9 \times 10^5$ viable microorganisms per gram of the viable microorganisms composition of *Bacillus subtilis* for poultry prepared in Production Example 5, were used in the starting stage (from 5 to 21 days after hatching) and during the period of from the grower stage (from 21 days to 43 days after hatching) to the finishing stage (from 43 days to the day of shipping), respectively. Other feed management was carried out in accordance with the feeding method of chickens conventionally carried out in poultry farms. The results of the test are shown in Table 3.

COMPARATIVE EXAMPLE 2

The feeding was carried out in the same manner as described in Example 2, except that the "Starting AT (Zenki AT)" for starting stage use and the "Grower AT (Kohki AT)" for grower stage use were used in the starting stage and grower stage, respectively, and the viable microorganism composition of *Bacillus subtilis* was not provided throughout the whole stages. The results are shown in Table 3.

TABLE 3

| | Comp. Example 2 | Example 2 | Ratio |
|---|---|---|---|
| The number of set chicks | 8,300 | 8,300 | 100 |
| Body weight of chicks (g/chick) | 43.6 | 43.6 | 100 |

TABLE 3-continued

|  | Comp. Example 2 | Example 2 | Ratio |
|---|---|---|---|
| Age when shipped (days) | 54 | 55 | 102 |
| The number of chicks per tsubo | 59.3 | 59.3 | 100 |
| Average body weight (kg/bird) | 2.886 | 2.838 | 98 |
| Rate of raising (%) | 95.7 | 97.0 | 101 |
| Feed conversion ratio | 2.007 | 2.048 | 102 |
| Production score | 255 | 244 | 96 |
| Body weight gain (g/day · chick) | 53.4 | 51.6 | 97 |

Since drug-free feed was used in and after the starting stage in Example 2, while drug-containing feed was used in Comparative Example 2, the body weight gain in the former case was slightly inferior with a value of 51.6 g/day·chick, but the rate of raising was 97% which was excellent and the production score was 244, thus showing economical production results.

EXAMPLE 3

Field effect test III (test with no drugs)

The test was carried out using Chunky (Brand name, Commercial strain). Chicks (0 day after hatching) in a chick-carrying cage were spray-provided with 40 g of the viable microorganism composition of lactic acid bacteria for poultry prepared in Production Example 4 (total number of lactic acid bacteria: $2.0 \times 10^{10}$ viable microorganisms per gram) which had been uniformly suspended in 4 kg of pure water. As the provision feed, the "Starting AT (Zenki AT)" for starting stage use from which antibiotics had been removed and the "Brogoal A" for finishing use, which had been mixed with $9 \times 10^5$ viable microorganisms per gram of the viable microorganism composition of *Bacillus subtilis* for poultry prepared in Production Example 5, were used during the period of from the start feeding stage to the starting stage (from 0 to 21 days after hatching) and during the period of from the grower stage to the finishing stage (from 21 days to the day of shipping), respectively. Other feed management was carried out in accordance with the feeding method of chickens conventionally carried out in poultry farms. The results of the tset are shown in Table 4.

COMPARATIVE EXAMPLE 3

The feeding was carried out in the same manner as described in Example 3, except that the "Starting AT (Zenki AT)" for starting stage use, the "Grower AT (Kohki AT)" for grower stage use and the "Brogoal A" for finishing use were respectively used as the feed during the period of from the start feeding stage to the starting stage, in the grower stage (from 21 to 43 days after hatching) and in the finishing stage (from 43 days to the day of shipping), respectively, and the viable microorganism composition of *Bacillus subtilis* was not provided throughout the whole stages. The results are shown in Table 4.

TABLE 4

|  | Comp. Example 3 | Example 3 | Ratio |
|---|---|---|---|
| The number of set chicks | 7,220 | 7,220 | 100 |
| Body weight of chicks (g/chick) | 41.5 | 44.9 | 108 |
| Age when shipped (days) | 54 | 55 | 102 |
| The number of chicks per tsubo | 51.6 | 51.6 | 100 |
| Average body weight (kg/bird) | 2.768 | 2.805 | 101 |

TABLE 4-continued

|  | Comp. Example 3 | Example 3 | Ratio |
|---|---|---|---|
| Rate of raising (%) | 97.1 | 97.0 | 100 |
| Feed conversion ratio | 2.017 | 2.020 | 100 |
| Production score | 247 | 245 | 99 |
| Body weight gain (g/day · chick) | 51.3 | 51.0 | 99 |

The test of Example 3 was not carried out at the same time with the test of Comparative Example 3 but after completion of the feeding of Comparative Example 3, and, since a cold wave hit the field during the feeding period of Example 3, the final growth and rate of raising in Comparative Example 3 were influenced by the cold wave. However, although feeding was carried out without administering antibiotics and antibacterial agents throughout the whole period, production results of Example 3 were identical to those of Comparative Example 3.

Also, comparative tests corresponding to Examples 1 to 3, in which feeding was carried out without drugs and without administering the viable microorganism composition of lactic acid bacteria for poultry and the viable microorganism composition of *Bacillus subtilis* for poultry, were not carried out, because normal growth cannot be obtained under such feeding conditions.

EXAMPLE 4

In Example 3 and Comparative Example 3, fresh droppings of chickens were collected on the day before shipping and, using droppings of three birds as one sample, the coliform group and bacteria of the genus Salmonella in the droppings were measured. The results are shown in Table 5. In this case, serotype of every bacteria of the genus Salmonella was O7.

TABLE 5

|  |  | Chicken of Comp. Example 3 | Chicken of Example 3 |
|---|---|---|---|
| Bacterial count per 1 g droppings (logarithmic value) | Entero-bacteriaceae | 7.32 ± 0.53 | 6.93 ± 0.52** |
|  | Salmonella | 3.54 ± 0.80 | 3.07 ± 0.69 |
| Detected case of Salmonella/total case |  | 18/29 | 9/30* |

*p < 0.05
**p < 0.01

In comparison with Comparative Example 3, the coliform group decreased significantly in Example 3, and detection ratio of bacteria of the genus Salmonella was also reduced significantly.

EXAMPLE 5

Comparison was made on the palatability of the meat of the chickens raised in Example 3 and Comparative Example 3. Since accurate sensory test cannot be carried out when the meat itself is subjected to the tset due to various treating factors, whole chicken soup was prepared and subjected to the sensory test. The gutting III (edible part remained after sacrifice and bleeding and subsequent removal of feather, head, toes and organs) was used in the test as the whole chicken, and one part by weight of the sample was mixed with 4 parts by weight of water and 1.8% of salt and boiled for 2 hours. After filtration of the mixture through bleached cotton, the filtrate (soup) was prepared to three times the weight of the tested chicken to adjust the soup concentration. The thus obtained soup samples were subjected to the sensory test in which 38 panelists were allowed to select the most delicious sample. The results are shown in Table 6.

TABLE 6

|  | The number of panelists who selected | Selection ratio |
|---|---|---|
| Chicken of Example 3 | 33 | 0.868** |
| Chicken of Comp. Example 3 | 5 | 0.132 |

**p < 0.01

In comparison with the chicken of Comparative Example 3, the chicken of Example 3 was selected for its palatability by a considerably large number of panelists, thus confirming the delicious nature of chicken produced through drug-free feeding.

In this connection, in an itemized flavor evaluation carried out at the same time, good evaluations were obtained for the soup of the chicken of Example 3, statistically significant with a significance level of 1%, on each of (1) preference, (2) richness taste and (3) suitable taste.

REFERENCE EXAMPLE 1

Completely drug-free test solely by viable microorganism composition of *Bacillus subtilis* for poultry The test was carried out using Chunky poultry in a district where broilers were fed in large numbers. As the provision feed, "Broiler Gold Starting Crumble (Broiler Gold Zenki Crumble)" from which antibiotics had been removed and "Broiler Finisher (Broiler Shiage)" (containing no antibiotics and the like) (both manufactured by Shikoku Haigo Shiryo, Co.), each of which had been mixed with $1 \times 10^6$ viable microorganisms per gram of the viable microorganism composition of *Bacillus subtilis* for poultry prepared in Production Example 5 and enriched with vitamins and minerals, were used during the period of from the start feeding stage to the starting stage (from 0 to 21 days after hatching) and during the period of from the grower stage to the finishing stage (from 21 days after hatching to the day of shipping), respectively. Other feed management was carried out in accordance with the feeding method of chickens conventionally carried out in poultry farms. The results of the test are shown in Table 7.

COMPARATIVE EXAMPLE 4

Feeding was carried out in the same manner as in Reference Example 1, except that "Broiler Gold Starting Crumble (Broiler Gold Zenki Crumble)" (containing antibiotics), "Broiler S" (containing antibiotics) and "Broiler Finisher (Broiler Shiage)" (each of which manufactured by Shikoku Haigo Shiryo, Co.) were used as the feed during the period of from the start feeding stage to the starting stage, in the grower stage (from 21 to 32 days after hatching) and in the finishing stage (from 32 days after hatching to the day of shipping), respectively, and the viable microorganism composition of *Bacillus subtilis* was not provided. The results are shown in Table 7.

TABLE 7

|  | Comp. Example 4 | Reference Example 1 | Ratio |
|---|---|---|---|
| The number of set chicks | 6,800 | 6,800 | 100 |
| The number of shipped birds | 6,571 | 6,662 | 101 |
| Rate of raising (%) | 96.6 | 98.0 | 101 |
| Age when shipped (days) | 39.6 | 41.0 | 104 |
| Average body weight (kg/bird) | 1.71 | 1.58 | 92 |
| Feed conversion ratio | 2.03 | 2.22 | 109 |
| Production score | 205 | 170 | 83 |

A higher rate of raising was obtained in Reference Example 1 than that in Comparative Example 4, but the body weight gain delayed in the starting stage of feeding and the delay left a trail to the end, so that the body weight gain was low throughout the feeding period as a result thereof and was not a commercially acceptable level.

Also, a drug-free raising test by providing only the viable microorganism composition of lactic acid bacteria for poultry without administering the viable microorganisms composition of *Bacillus subtilus* for poultry was not carried out, because such a test can be carried out only in a place where environmental pollution does not exist such as an experimental facility under complete sanitary conditions but not in the field of intensive poultry farms.

INDUSTRIAL APPLICABILITY

Since the administration of a viable microorganism composition for poultry comprising specific viable lactic acid bacteria is carried out at a specified stage in combination with the administration of a viable microorganism composition for poultry comprising viable *Bacillus subtilis*, the method of the present invention for the administration of the viable microorganism compositions for poultry can exerts various effects, such as inhibition of the growth of toxic bacteria, prevention of diarrhea, enhancement of growth, improvement of the feed conversion ratios and the like, and also renders possible drug-free feeding of chickens with high productivity and, particularly in the case of edible chickens, production of delicious and safe meat and eggs with high productivity. Consequently, the method of the present invention for the administration of the viable microorganism compositions for poultry is useful for the feeding of edible birds, such as chicken, particularly broilers, and the like.

Obviously, numerous modifications and variations of the present invention are possible in light of the above-teachings. It is therefore to be understood that within the scope of the appended claims, the invention may be practiced otherwise than as specifically described herein.

The priority document of the present application, Japanese Patent Application No. Hei. 9-145372, filed on Jun. 3, 1997, is hereby incorporated by reference.

What is claimed is:

1. A method for administering a viable composition of microorganisms to poultry, comprising:
   administering an effective amount to inhibit the growth of *C. campylobacter* a first composition to a poultry comprising viable bacteria belonging to *Lactobacillus reuteri* and *Lactobacillus johnsonii*, at the stage of newborn fledgling; and
   administering an effective amount to inhibit the growth of *C. campylobacter* a second composition to said poultry comprising a viable microorganism belonging to *Bacillus subtilis*, wherein antibiotics are not administered to said poultry during at least the grower stage and finishing stage of said poultry.

2. The method according to claim 1, wherein said first composition is administered within 4 days after hatching of said poultry.

3. The method according to claim 1, wherein said first composition is administered within 2 days after hatching of said poultry.

4. The method according to claim 1, wherein said *Lactobacillus reuteri* is at least one member selected from the group consisting of (a) *Lactobacillus reuteri* CP-720, Deposit No. FERM BP-6332, and a mutant thereof, (b) *Lactobacillus reuteri* CP-722, Deposit No. FERM BP-6334, and a mutant thereof.

5. The method according to claim 1, wherein said *Lactobacillus johnsonii* is *Lactobacillus johnsonii* CP-721, Deposit No. FERM BP-6333, or a mutant thereof.

6. The method according to claim 1, wherein said first composition further comprises a carrier or diluent.

7. The method according to claim 1, wherein said first composition further comprises a poultry feed.

8. The method according to claim 1, wherein said first composition is administered orally.

9. The method according to claim 1, wherein said first composition is administered by spraying.

10. The method according to claim 1, wherein said first composition comprises from $10^6$ to $10^{10}$ of said bacteria per gram.

11. The method according to claim 1, wherein $1\times10^3$ to $1\times10^{10}$ of said bacteria are administered to said poultry.

12. The method according to claim 1, wherein said first composition is administered only once or twice.

13. The method according to claim 1, wherein said *Bacillus subtilis* is *Bacillus subtilis* C-3102, Deposit No. FERM BP-1096, or a mutant thereof.

14. The method according to claim 1, wherein said second composition further comprises a carrier or diluent.

15. The method according to claim 1, wherein said second composition further comprises a poultry feed.

16. The method according to claim 1, wherein said second composition is administered orally.

17. The method according to claim 1, wherein said second composition comprises from $10^5$ to $10^8$ of said viable *Bacillus subtilis* per gram.

18. The method according to claim 1, wherein said second composition is administered after the administration of said first composition.

19. The method according to claim 1, wherein said poultry is a chicken, a duck, a goose, a quail, a wild duck, an ostrich or a pet bird.

20. The method according to claim 4, wherein said *Lactobacillus johnsonii* is *Lactobacillus johnsonii* CP-721, Deposit No. FERM BP-6333, or a mutant thereof, and said *Bacillus subtilis* is *Bacillus subtilis* C-3102, Deposit No. FERM BP-1096, or a mutant thereof.

21. The method of claim 1, wherein said first composition is administered in the absence of antibiotics.

22. The method of claim 1, wherein said second composition is administered in the absence of antibiotics.

23. The method of claim 1, wherein said first composition and said second composition are administered in the absence of antibiotics.

* * * * *